United States Patent [19]

Serpelloni et al.

[11] Patent Number: 5,573,777
[45] Date of Patent: Nov. 12, 1996

[54] PULVERULENT MANNITOL OF MODERATE FRIABILITY AND PROCESS FOR ITS PREPARATION

[75] Inventors: Michel Serpelloni, Beuvry les Bethune; Jean-Philippe Boonaert, Laventie, both of France

[73] Assignee: Roquette Freres, Lestrem, France

[21] Appl. No.: 311,791

[22] Filed: Sep. 26, 1994

[30] Foreign Application Priority Data

Sep. 28, 1993 [FR] France .................. 93 11513

[51] Int. Cl.⁶ .................................. A61K 9/14
[52] U.S. Cl. .................................. 424/440; 424/489
[58] Field of Search ...................... 424/400, 440, 424/489, 499; 514/960, 738, 777; 426/103; 536/4.1, 124, 18.5

[56] References Cited

U.S. PATENT DOCUMENTS

| | | | |
|---|---|---|---|
| 3,145,146 | 8/1964 | Liebermann | 514/772 |
| 3,341,415 | 9/1967 | Scott | 514/960 |
| 4,293,570 | 10/1981 | Vadasz | 426/103 |
| 4,661,647 | 4/1987 | Serpelloni et al. | 568/868 |
| 5,160,680 | 11/1992 | Serpelloni et al. | 568/868 |

FOREIGN PATENT DOCUMENTS

| | | |
|---|---|---|
| 55-36646 | 9/1980 | Japan . |
| 61-85330 | 4/1986 | Japan . |
| 61-85331 | 4/1986 | Japan . |

OTHER PUBLICATIONS

Jinot et al., Chemical Abstracts, vol. 105, 1987, #48934.

*Primary Examiner*—Thurman K. Page
*Assistant Examiner*—P. Webber
*Attorney, Agent, or Firm*—Henderson & Sturm

[57] ABSTRACT

The invention relates to a relatively pure pulverulent mannitol, having a moderate and not excessive friability of between 40 and 80% in a Test I, a low apparent density of between 300 and 525 g/l for a particle size cut of between 100 and 200 microns and, additionally, a specific particle size in the sense that it contains less than 30% of particles with a size of less than 75 microns. This pulverulent mannitol possesses remarkable functional properties which make its use particularly recommended as sweetening agent, texturizing agent or additive excipient or vehicle in the food and pharmaceutical industries.

28 Claims, No Drawings

PULVERULENT MANNITOL OF MODERATE FRIABILITY AND PROCESS FOR ITS PREPARATION

FIELD OF THE INVENTION

1. Technical Field

The present invention is directed to a pulverulent mannitol of moderate friability additionally having a low density and a specific particle size.

The present invention is also directed to a process for the manufacture of the said mannitol.

2. Discussion of Background and/or Material Information

The pharmaceutical industry consumes large tonnages of sucrose and lactose. These are especially used as excipients in dry forms which are, for example, gelatin capsules, soluble powders, pulverulent nutrient preparations and tablets. These sugars are also employed in the crystalline form in the industrial preparation of drinkable solutions and suspensions.

The food industry, for its part, also uses significant amounts of sucrose for similar reasons, either in the crystalline state in dry forms which are sugar-containing foods to be dispersed and diluted such as, for example, powdered drinks and desserts, or in the dissolved state, such as during the preparation of liquid drinks.

Moreover, sucrose finds a certain use as a vehicle in various industries such as that of additives intended in particular for the food and pharmaceutical fields. These additives can be flavours, dyes, strong sweeteners, vitamins, active principles or alternatively protein substances such as amino acids and enzymes.

Many consumers nowadays, being more worried than in the past about their diet, avoid consuming sugars as much as possible. In order to respond to this expectation, manufacturers have developed sugar-free formulations in which use is made, as a sweetening agent, of strong sweeteners or else of polyols, whose reduced caloricity and whose harmlessness with respect to teeth are today clearly established.

As regards the field with which the present invention will be specifically concerned, namely pharmaceutical excipients, bulk sweeteners used in the food industry and additive vehicles, a number of pulverulent polyols are already commonly used. More precisely, they are sorbitol, xylitol and mannitol.

Sorbitol has the advantage of being the cheapest of these three polyols. This explains why it is so frequently used. It is an excellent excipient, especially in compression, due to its specific ability to crystallize in the form of directly compressible needle-shaped crystals.

However, it is criticized for being, even when it has crystallized in its stablest form, more hygroscopic than sugar. Thus it is that its flow becomes difficult, indeed impossible, as soon as an uptake in water is involved. In order to avoid this problem, a coarser particle size is sometimes retained but then the dissolution times of the powder generally become excessively lengthy. Nevertheless, even when acting in this way, the high hygroscopic nature of sorbitol in comparison with sugar prohibits the use of this polyol in all cases when it is combined with active principles or ingredients which are very sensitive to water.

Xylitol, for its part, is rarely used as an excipient outside the manufacture of tablets. This is explained by its high price but also by the fact that it has a tendency, even more easily than sorbitol, to set solid under normal moisture conditions.

Mannitol, due to the low hygroscopicity of its crystalline form, could constitute an excellent excipient. Unfortunately, the product obtained by crystallization in water from a supersaturated solution always has an excessive friability. The very low mechanical strength of the particles gives the product a tendency to crumble and therefore to be reduced to a dust during conveyance, mixing or alternatively transportation. The fine particles created by these mechanical actions are a source of not-insignificant contamination in manufacturing plants but can also be the source of explosions. Moreover, the already mediocre flow properties of mannitol which has crystallized in water, due to the orthorhombic structure of its crystals, become particularly bad when the latter contains these fine particles. This harms the filling and emptying of feed chutes and hoppers in particular but also of packing bags and of single-dose sachets intended for patients and consumers. Moreover, mannitol obtained by crystallization in water has, due to its very compact crystalline structure, a low ability to dissolve. This is the case even when the product is finely milled because the particles then become electrostatically charged and form agglomerates which only dissolve very slowly. This low rate of solubilization, although judged to be an advantage in certain specific applications, is, in the cases which are of concern here, always regarded as a major disadvantage forming an obstacle to its use. Other pulverulent forms of mannitol as well as the means for obtaining the latter are described in the literature. In particular, the following documents are known:

French Patent No. 2,571,045, commonly owned with the present invention, relates to a directly compressible mannitol obtained by treating by centrifugal turbine action from a molten product. It describes the characteristics of this product in comparison with other mannitol powders of the prior art obtained by wet granulation. It appears that all the products which are dealt with in this document always have a very coarse particle size and, for this reason, have a low ability to dissolve. Moreover, the products obtained according to these processes have a very low friability, of between 45 and 81%, according to the very severe test used. As it has been observed, it is very difficult to modify and to adjust this characteristic by acting on the manufacturing parameters of the process described.

French Patent No. 2,571,046, commonly owned with the present application, is directed to a process for the preparation of directly compressible granular mannitol. The product obtained in that way is also coarse since it has a mean diameter of 620 microns. It is certainly possible to adjust the particle size of the product by carrying out a finer milling and by then carrying out a sieving but the manufacturing yield then significantly decreases, so much so that the cost price of the product becomes exorbitant. On the other hand, it is not possible to adjust the friability of the powder obtained according to this process. In fact, the latter only makes it possible to prepare products with a very low friability which is always less than 80% in the particularly severe test shown, as has been verified by the Applicant Company.

U.S. Pat. No. 3,341,415, relates to a method for the preparation of a pharmaceutical excipient containing at least 20% mannitol and an additional sugar chosen from lactose, sucrose, erythritol, galactose and sorbitol. The principle consists in melting the binary mixture composed of mannitol and the sugar used above their respective melting points and in then cooling the molten mixture obtained so as to solidify it in the form of fine droplets in cold air. A powder is thus obtained which has a mean diameter of between 50 and 200 microns. Besides the fact that the process described is very problematic to set up on an industrial scale, the product obtained is hygroscopic, very compact, has little friability and is very difficult to dissolve in water. It, therefore, does not have the characteristics desired in the context of the present invention.

U.S. Pat. No. 4,293,570, describes a process for the direct preparation of powders having a particle size of less than 20 microns. This process, which is similar to that described above, consists in spraying, in the form of droplets, a sweetener syrup having a very high solids content, of between 70 and 99.5%, and in cooling the droplets obtained in a stream of cold air so as to solidify them. It is said that the process may be suitable for mannitol, which is not very likely taking into account the particularly low solubility of this polyol in comparison with the other polyols mentioned. Nevertheless, even if the process described was successfully implemented, it would not make it possible to prepare dust-free mannitol powders having good flow properties, taking into account the very low size of the particles then obtained.

Japanese Patent Application JP 61-85331, is directed to a process for the preparation of excipients by direct compression, consisting in drying, by spraying, a mixture containing both D-mannitol and a starch hydrolysate. It emerges from this document that, with less than 5% starch hydrolysate, the excipient obtained according to this process, although weakly hygroscopic when it is placed at 75% relative humidity and at a temperature of 40° C., always has an excessively high content of particles with a size of less than 200 mesh (75 microns). This value, in the region of 70%, is lowered when the starch hydrolysate represents 15% and 25% of the excipient, but the latter then unfortunately becomes excessively hygroscopic and cariogenic and no longer corresponds to the definitions of the Pharmacopoeiae in force. In other words, this document does not teach the means of preparing a pulverulent mannitol containing few fine particles and which, moreover, is non-hygroscopic and non-cariogenic.

Japanese Patent Application JP 61-85330, relates to a process for the preparation of excipients, characterized in that it consists in drying, by spraying, D-mannitol without mixing it beforehand with a starch hydrolysate, in contrast to the above Application filed by the same company. It appears that the products obtained under these conditions contain, in the manner of the control products, more than 50% of particles with a size of less than 200 mesh (75 microns), which is harmful to a correct flow of the product.

Japanese Patent JP 80-36646, describes a process for the preparation of granulated powders of crystalline alcohol sugars, consisting in drying, by spraying, a suspension having at least 75% solids. A prior maturing for 3 to 24 hours at high temperature is necessary in order to lower the viscosity of the suspension. The process is only applied to sorbitol and xylitol. It is indicated that, under the same conditions, it may be suitable for other polyols such as mannitol but this is not very likely, taking into account the low solubility of the latter. By adjusting the conditions so that the process described becomes applicable to mannitol, the result thereof is that the process becomes particularly complex to set up industrially but also expensive due to the specific conditions for the preparation of the suspension. Moreover, the product obtained always contains a very high content of fine particles, like the product described in Japanese Patent Application JP 61-85330.

U.S. Pat. No. 3,145,146 describes a process for modifying the physical characteristics of mannitol, by virtue of a spray drying, and the product obtained in this way. A volatile solvent is used for this, preferably ethyl alcohol or chloroform, optionally containing a hydrogenated vegetable oil. This volatile solvent preferably contains a binder which can be a paraffin, a gum, or a cellulose derivative. This binder is introduced before atomization. A powder is thus obtained whose particle size is between 5 and 150 microns. It has been verified that the size of the particles according to this process is, just as with the JP 80-36646 and JP 61-85330 processes described above, always very low, so much so that the mean diameter of the particles is between 50 and 75 microns. This amounts to saying that at least 50% of the particles of the powder have, in all cases, a size of less than 75 microns, which is far from being ideal for obtaining a good flow and an absence of dust in plants.

Fortified by this observation, it has discovered that there has for many years existed an unsatisfied need regarding an excipient which would simultaneously have the, most often incompatible, advantages of being non-cariogenic and non-hygroscopic, of possessing good flow and dissolution properties and of not being the source of dust or of explosions in production or packaging plants. To obtain such an excipient possessing all the functional characteristics listed above, it has been observed that, contrary to all expectation, it was advisable to choose, from the polyols, a relatively pure mannitol and to modify its physical characteristics by employing an appropriate process so that it simultaneously has a moderate and not excessive friability, a centered particle size free of fine particles and a structure of very little density.

SUMMARY OF INVENTION

The present invention, therefore, relates to a relatively pure pulverulent mannitol, having:

a friability according to a Test I of between approximately 40% and approximately 80% an apparent density, for a particle size cut of 100 to 200 microns, of between approximately 300 and approximately 525 g/l, and less than approximately 30% of particles with a size of less than 75 microns.

The present invention also relates to a process for the manufacture of a pulverulent mannitol possessing the physical characteristics listed above, comprising an atomization stage of a mannitol solution or suspension and then a granulation stage by a wet route of the mannitol resulting from the said atomization stage.

DETAILED DESCRIPTION

"Relatively pure" is understood to mean a mannitol richness, calculated with respect to the amount of sugars or polyols present, of at least 90%. Sugars and polyols denotes, in the present invention, mono- and disaccharides in the hydrogenated or non-hydrogenated form.

It is particularly surprising that a product having the physical characteristics listed above can exist. In fact, it is normally the case with sugars such as, for example, sucrose and dextrose, or even for polyols, such as sorbitol, that the lower the apparent density of the pulverulent product in question, the more the latter becomes friable, that is to say sensitive to a detrimental change in its particle size by mechanical action.

As an example, sorbitol marketed by ROQUETTE FRERES, the assignee of the instant application, under the trademark NEOSORB® 20/60 DC has a high density and has a friability of 54% in the test described in French Patent No. 2,571,045, whereas an atomized sorbitol such as that marketed, for example, by the Company Merck under the trademark KARION® Instant, with a markedly lower density, for its part has, for a similar particle size and under the same measuring conditions, a higher friability, in the region of 75%.

Normally, therefore, an apparent density measurement makes it possible to have a good idea of the friability, given that friability and apparent density are always inversely related. This, surprisingly and unexpectedly, is not the case for a relatively pure mannitol. In fact, the friability of a pulverulent mannitol of low density and in accordance with the invention is, in contrast to what is observed for the products mentioned above, always at most equal to and generally less than that of mannitol powders, of compact and very dense structure, obtained by crystallization in water. Consequently, and contrary to what was expected, a pulverulent mannitol, even of very little density, can be used as vehicle or excipient due to its good mechanical strength. Moreover, it has, as such, better properties than a mannitol crystallized in water, which is judged as too friable.

In order to measure the first characteristic of the mannitol in accordance with the invention, namely the friability, Test I will be carried out. Test I consists in subjecting the particles to be tested to mechanical action in an apparatus known as a friabilimeter. Use is made, for this, of an apparatus of trademark ERWEKA TAP manufactured by the company ERWEKA (6056 Heusenstamm—F.R.G.), rotating at a uniform rotational speed of 25 revolutions/minute, and into which 5 identical steel balls with a diameter of 17 mm and with a weight of 18.87 g have been introduced. In order to carry out this Test I, an amount of 15 g of product having a particle size of between 100 and 200 microns is introduced into the crushing chamber of this friabilimeter and then the apparatus is set in rotational motion for 15 minutes.

At the end of the experiment, the proportion by weight represented by the residue retained on a sieve with a mesh size of 100 microns is determined.

The value of the friability corresponds to the percentage of powder not retained by the sieve defined above.

The friability is proportionally greater as the percentage of powder which is not retained by the above-said sieve becomes greater.

It should be noted that this test is based on the same principle as that described in French Patent No. 2,571,045 but is applied to a finer particle size cut. For this reason, it is, with respect to that described in this patent, markedly less severe, given that, for a given powder, a coarse particle size cut is alway more friable than a finer particle size cut.

The pulverulent mannitol in accordance with the invention has, in this Test I, a moderate and not excessive friability, that is to say of between approximately 40 and 80%. A product will be preferred having a friability of between 40 and 68% and better still between 45 and 65% in Test I.

As regards the second essential physical characteristic of the pulverulent mannitol in accordance with the invention, namely its apparent density, use is made for measuring it of an apparatus marketed by the company HOSOKAWA under the tradename "Powder Tester", by applying the method recommended for measuring an apparent density. Under these conditions, the mannitol in accordance with the present invention has a particularly low apparent density, that is to say of between approximately 300 and approximately 525 g/l, preferably 350 to 510 g/l and more preferentially between 400 and 495 g/l.

According to the third essential physical characteristic, the pulverulent mannitol in accordance with the invention has a very specific and centered particle size, so as to exhibit flow and dissolution properties characteristic of an ideal vehicle or excipient which does not generate dust in plants. It always contains less than approximately 30% of particles of less than 75 microns. The preferred pulverulent mannitol only contains less than 25%, indeed less than 15%, thereof, the ideal being, although this is more difficult to obtain, a pulverulent mannitol which does not contain more than 10% and better still does not contain more than 5% of particles of less than 75 microns.

Moreover, the pulverulent mannitol in accordance with the invention is preferably virtually free of particles of less than 40 microns, the latter being the most contaminating and the most explosive.

As regards the coarse particles present in the pulverulent mannitol in accordance with the invention, the latter preferably contains less than approximately 40%, more preferentially less than 30% and better still less than 20% of particles with a size greater than 250 microns. Ideally, the product in accordance with the invention is, as it were, free of particles with a size greater than 315 microns in order for its ability to dissolve in water to be excellent.

This pulverulent mannitol in accordance with the present invention can also be characterized by its mean diameter and its uniformity of particle size distribution. The latter, defined as being the ratio of the mesh through which 60% of the particles pass to that through which only 10% of the particles pass, is generally between 1 and 8 approximately, preferably between 1 and 5 and more preferentially still between 1 and 3. As for the mean diameter, it is preferably between 100 and 200 microns.

From the viewpoint of its chemical composition, the pulverulent mannitol in accordance with the present invention is relatively pure, that is to say that it has a high mannitol richness. It has been verified that this constituted a *sine qua non* condition for obtaining a vehicle or excipient which is stable and which has little hygroscopicity. This mannitol richness, calculated with respect to the amount of sugars or polyols present, will be at least 90%, preferably greater than 95% and more preferentially greater than 98.5%, the ideal being to approach the value of 100% as far as possible.

Moreover, the pulverulent mannitol in accordance with the present invention generally contains very small amounts of water. This content is preferably less than 1% and more preferentially still less than 0.3%.

Moreover, the pulverulent mannitol of the present invention can comprise substances other than sugars or polyols in a more or less significant amount depending on the destination intended for it.

Mention may be made, among substances capable of forming part of the pulverulent mannitol composition, of dyes, flavours, fragrances, pharmaceutical or veterinary principles, preservatives, acids and their salts, strong sweeteners, vitamins, fats, protein substances, such as amino acids, enzymes or alternatively gelatins, gums such as gum arabic and gum tragacanth, gum bases of chewing-gum type, cellulose fibres, cellulose and its derivatives such as, for example, hydroxypropyl methyl cellulose, pectins, inulin and its derivatives, starches and starch hydrolysates of low dextrose equivalent, which are optionally hydrogenated, or yet again inorganic compounds.

In the case where, for one reason or another, these substances would be introduced into the product in accordance with the invention, very attentive care will then be applied to the choice of the latter, preferably retaining those of them which would not be capable of greatly detrimentally affecting the three essential physical characteristics of the pulverulent mannitol in accordance with the invention defined above, or alternatively of detrimentally affecting the advantageous property of the mannitol of being both non-cariogenic and having little hygroscopicity.

As regards the functional characteristics of the pulverulent mannitol in accordance with the present invention, its ability to flow has been evaluated by using the apparatus marketed by the company HOSOKAWA. This apparatus makes it possible to measure, under standardized and reproducible conditions, the ability to flow of a powder and to calculate a flow grade, also known as the Carr index. The mannitol in accordance with the invention normally has an excellent flow grade, of between 70 and 90. This value is preferably between 75 and 90 and more preferentially between 80 and 90. This value is very similar to those of mannitol powders of the prior art obtained by wet granulation or alternatively by extrusion of crystals obtained by crystallization in water. This is all the more remarkable since, with respect to these prior products, the pulverulent mannitol in accordance with the invention has a markedly finer particle size.

Moreover, the ability of the product to flow, forming the subject of the present invention, is normally markedly greater than those of mannitol powders obtained by simple crystallization in water or simple atomization.

Without wishing to be constrained by any one theory, it may be thought that the excellent ability to flow of the mannitol of the invention is explained by the combination of a number of its physicochemical characteristics, namely in particular its centered particle size, the absence of significant electrostatic charges at the surface of the particles constituting it, its mannitol richness, its low hygroscopicity and finally the characteristic shape of the particles constituting it. As regards this last point, it should be noted that, in fact, the pulverulent mannitol in accordance with the invention comprises particles of variable shape which are always free of sharp edges and which are composed of a multitude of microparticles agglomerated to each other. Under a microscope, it is easily differentiated from a mannitol crystallized in water consisting of particles, in the form of layers, with a substantially constant thickness but of variable length and width. It is also differentiated from a mannitol obtained by simple atomization composed of essentially spherical particles, or alternatively from an extruded product comprising angular particles in the form of fairly regular blocks.

A second essential functional property of the pulverulent mannitol in accordance with the present invention is that of dissolving very quickly in water. In order to measure this rate of dissolution, a Test II is carried out which consists in introducing, into 150 grams of demineralized and degassed water maintained at 20° C. and subjected to stirring at 200 r/minute in a 250 ml low form beaker, exactly 5 grams of a particle size cut of 100 to 200 microns of the product to be tested. The dissolution time corresponds to the time necessary, after introduction of the particle size cut, to obtain perfect visual clarity of the suspension thus prepared. Under these conditions, the pulverulent mannitol in accordance with the invention generally has a rate of dissolution of less than 30 seconds. The preferred product dissolves in less than 25 seconds whereas the ideal product requires a time of less than 20 seconds. These times are generally less than those obtained with all the mannitol powders currently marketed.

A third very advantageous property for bagging and use of pulverulent mannitol in accordance with the present invention is that of producing very little dust, although its particle size is rather fine in comparison with the products described in French Patents FR 2,571,045 and FR 2,571,046. This tendency to produce or not to produce dust can be easily measured by using the HOSOKAWA apparatus already described above and by measuring the dispersibility of the product to be tested as indicated in the directions for use relating to this apparatus.

Under these conditions, the pulverluent mannitol in accordance with the present invention has a dispersibility generally of between 10 and 30 and preferably of between 10 and 25, which denotes a very low tendency to generate dust. It may be observed that the product of the invention has, in this respect, characteristics which are as good as those of the extruded or granulated powders of mannitol crystallized beforehand in water and with a coarse particle size. In contrast, its tendency to produce dust is markedly less than those of powders obtained by simple crystallization in water or by simple atomization, as that described in Patent JP 61.85330.

Moreover, other, not insignificant, advantages for the use of the pulverulent mannitol in accordance with the present invention should also be pointed out. These advantages, like those described above, are also characteristic of it, in the sense that a simple particle size cut of the products of the prior art does not simultaneously possess all these properties. Mention may be made, among these advantages, of its very good ability to be mixed as a powder with other products, its very good resistance to demixing or to particle segregation when it is mixed, for example, with a particle of a finer particle size, and its good ability to be compressed in order to prepare chewable tablets.

The pulverulent mannitol in accordance with the present invention is capable of being obtained by carrying out an atomization stage of a solution or suspension which is relatively pure in mannitol with respect to the amount of sugars or polyols present in the solution or suspension, and then a granulation stage by a wet route of the mannitol resulting from the atomization stage. It should be specified, as it has been observed, that the product in accordance with the invention cannot be prepared by simple atomization, as this has already been carried out, nor even by the granulation of mannitol crystals obtained by crystallization in water or in another solvent such as alcohol.

It has been observed, surprisingly and unexpectedly, that the combination of an atomization and of a granulation contrarily made it possible, by the use of known techniques applicable to mannitol, to adjust the friability so that it is high but not excessive and to adjust the density but also to prepare, with a high yield, a product in accordance with the invention as regards its particle size.

In fact, the processes described previously do not make it possible to obtain all the desired characteristics.

In order to carry out the atomization, use is preferably made of a syrup in the form of a suspension or else of a solution containing, on the one hand, water so that the solids content is between 20 and 70%, preferably between 20 and 60% and, on the other hand, mannitol with a richness greater than 90%, preferably greater than 95% and more preferentially greater than 98.5%.

Ordinarily, the syrup, having a temperature of between 20° and 100° C., is then atomized by using a conventional atomizer known to those skilled in the art and by generally choosing an inlet temperature of between 180° and 350° C. and a flow rate such that the temperatures of the air and of the atomized product at the outlet are both between 70° and 130° C.

It will be noted that the syrup intended to be atomized can also comprise substances other than sugars or polyols, especially when these substances are not prone to thermal degradation.

It will also be noted that in order to increase the efficiency and the productivity of the atomizer, recourse may advantageously be made to a syrup in the form of a suspension having a solid content of 50 to 70% and containing an elevated proportion of mannitol in the solid state. This suspension may be micronized and/or heated without difficulty up to 140° C., taking into account the very high chemical stability of mannitol, in such a manner as to adjust at the inlet of the atomizer, the size and the proportion of particles of mannitol.

The atomized powder is then granulated by employing either water or steam, or a mannitol syrup, or alternatively, although this is not preferred, a syrup comprising a binder such as a polyvinylpyrrolidone, a gum arabic, a hydroxypropyl methyl cellulose, a maltodextrin, a pregelled starch, a gelatin or any other binder known by those skilled in the art to possess the required properties.

In the case of the use of water, the appropriate water content is generally of the order of 10 to 20% but can vary with the particle size of the atomized powder.

In the case of the use of a syrup comprising a binder, the latter represents from 0.1 to 15%, preferably from 0.5 to 4%, of the solids content of the pulverulent mannitol in accordance with the invention.

In this case, a binder is preferably chosen which is incapable of detrimentally affecting the particularly advantageous property of the mannitol of not being cariogenic. The simplest, and preferred, way of managing it is to use, as binder, the same syrup as that intended for the atomization, as is made possible by certain industrial apparatuses where an atomization and then a granulation are successively carried out.

The pulverulent mannitol in accordance with the present can advantageously be employed, due to the quality of its functional properties mentioned above, as sweetening agent, texturizing agent or additive excipient or vehicle, in particular in the food and pharmaceutical fields.

It is also possible to use the mannitol according to the present invention in several other industries. For example, it can serve as a basic product for the preparation of chemical products such as, for example, fire-proofing substances, polyurethane foams, antifreeze solutions, surfactants, as a plastifying product or as a filler, such as for example, in plastics, paints, resins, rubber or paper, or yet again as products to be used as vehicles for example for veterinary or phytosanitary principles, industrial enzymes, fertilizers, oligo-elements, pesticides, active products permitting the destruction of rodents or of noxious mammals. Many other utilizations of pulverulent mannitol according to the invention are evidently envisageable and permitted thanks to the optimization of its very advantageous functional properties described above.

The invention will be even better understood using the examples which follow, which constitute a statement of certain advantageous embodiments and properties of the pulverulent mannitol according to the invention.

EXAMPLE 1

Preparation of a Pulverulent Mannitol in Accordance With the Invention

An aqueous mannitol solution containing 40% of material is prepared by dissolving, at 75° C., mannitol crystals obtained by crystallization in water.

This solution, maintained at 75° C., is atomized by employing a pilot apparatus marketed by the company NIRO under the name of Minor Mobile.

The inlet temperature is set at 280° C. and the flow rate is adjusted so that the outlet temperature is in the region of 120° C.

The atomized powder obtained is then granulated by using a syrup identical to that entering into the atomizer and then dried by a stream of hot dry air. There is thus obtained a pulverulent mannitol having the following characteristics:

a mannitol richness of 98.9%
a water content, measured by Karl Fischer, of 0.1%
a friability, according to Test I described above, of 44%
an apparent density of 457 g/l
the following particle size spectrum:
- particles with a size of less than 75 microns: approximately 3%
- particles with a size of less than 40 microns: traces
- particles with a size greater than 350 microns: traces
- particles with a size greater than 250 microns: approximately 1%
- particles with a size greater than 200 microns: approximately 2%
- particles with a size greater than 100 microns: approximately 86% a mean diameter: approximately 135 microns
a uniformity of distribution in the region of 1.5
a flow grade or Carr index of 79
a packed density of 549 g/l
a rate of dissolution, according to Test II, of 26 seconds
a dispersibility, according to the HOSOKAWA test, of 22%

The pulverulent mannitol in accordance with the invention has the properties of a good excipient, namely has a moderate and not excessive friability, a good ability to flow and a very high rate of solubilization. This excipient has the advantage of being neither cariogenic nor hygroscopic.

Moreover, the pulverulent mannitol thus obtained makes it possible easily to obtain tablets by using magnesium stearate at a level in the region of 2%.

EXAMPLE 2

Comparison of Products in Accordance With the Invention and Products of the Prior Art Other pulverulent products in accordance with the invention are prepared by applying the process described in Example 1 but slightly modifying the atomization temperatures, the incoming solids content, and flow rates and also the granulation conditions so as to obtain a range of samples.

The products obtained have the characteristics listed in the table below.

|  | Products in accordance with the invention | Standard mannitol (crystallized in water) | Mannitol according to FR-2,571,045 | Mannitol according to FR-2,571,046 | Granulated mannitols described in FR-2,571,045 | Mannitols described in JP-61-85330 |
|---|---|---|---|---|---|---|
| ERWEKA friabilities | | | | | | |
| • 100–200 micron cut (Test I) | 40 to 68% | 45–70% | 20% | 25% | 38% | impossible to measure |
| • 400–500 micron cut (Test of Patent FR 2,571,045) | 95 to 100% | impossible to measure | 45% | 75% | 70 to 81% | impossible to measure |
| Apparent densities (g/l) | | | | | | |
| • 100–200 micron cut | 300 to 525 | 525 to 560 | 550 to 590 | 570 to 620 | 515 to 530 | impossible to measure |
| • Commercial product | 300 to 600 | 470 to 520 | 650 to 750 | 650 to 740 | 650 to 750 | 500 to 600 |
| Particles | | | | | | |
| • Less than 40 microns | 10% max. | 40% | traces | traces | 5% | 30 to 70% |
| • Less than 75 microns | 30% Max. | 60% | traces | traces | 8% | 56 to 89% |
| • Greater than 250 microns | 40% max. | 15% | 99% | 90% | 80% | — |
| • Greater than 315 microns | traces | 5% | 60 to 90% | 50% | 75% | — |
| Mean diameters in microns | 100 to 200 | less than 75 | 520 to 620 | 400 to 650 | 650 to 860 | less than 75 |
| Flow grades over 100 (Carr index) | 70–90 | 50 | 85 | 85 | 82–85 | less than 55 |
| Dissolution times in seconds (Test II) | less than 30 | 20 to 35 | — | 50 to 75 | greater than 110 | 40 to 60 |
| Tendency to form dusts (HOSOKAWA dispersibility) | 10–30% | 15 to 55% | 5 to 15% | 5 to 15% | 5 to 20% | 30 to 70% |

The products in accordance with the invention, in contrast to the products of the prior art, all possess excellent functional properties, thus making them capable of being used without disadvantage as non-cariogenic and non-hygroscopic excipients and vehicles of additives, in particular in the food and pharmaceutical industries.

EXAMPLE 3

Comparison of Tablets Obtained by Employing Pulverulent Mannitol According to the Invention With Those Obtained According to the Prior Art Different tablets are prepared having concave faces of a thickness of 5 mm and a diameter of 20 mm by using a FETTE P 1000 press while exerting a compression force of 55 kN.

For this, the following pulverulent products are used, containing 1% of magnesium stearate:

Product I: granulated sucrose ALVEOSUCRE® by Béghin Say (France)
Product II: lactose monohydrate in the α form, TABLETOSE® from Meggle (Germany)
Product III: lactose monohydrate in the a form, atomized, FAST FLO® from FMC (USA)
Product IV: anhydrous lactose in the α form, DC LACTOSE 30 from D.M.C. (Holland)
Product V: Pulverulent mannitol according to the invention described in the example 1.

The strength of the tablets obtained is measured with the aid of a hardness testing device sold under the name TB24 by the company ERWEKA. The results obtained are shown in the table below.

| PRODUCTS No. | ACCORDING TO PRIOR ART | | | | INVENTION |
|---|---|---|---|---|---|
| | I | II | III | IV | V |
| Strength of tablets in N | 50 | 39 | 71 | 52 | 78 |

It is noted that the product according to the invention permits the advantageous obtention of harder tablets than with the different compressible products based on lactose or on sucrose currently utilized in this application.

The pulverulent mannitol according to the invention constitutes an excellent directly compressible product, as opposed to mannitol crystallized in water, and is also an excellent excipient for diverse active ingredients, notably those sensitive to humidity such as, for example, certain enzymes or vitamins.

We claim:
1. Pulverulent mannitol having:
   (a) a friability according to a Test I of between about 40% and about 80%, said Test I comprising subjecting about

15 g of pulverulent mannitol to be tested, having a particle size within a range of about 100 and about 200 microns, for about 15 minutes to mechanical action in a ERWEKA TAP friabilimeter, rotating at a uniform rotational speed of 25 revolutions per minutes, into which 5 substantially identical steel bells with a diameter of about 17 mm and with a weight of about 18.87 g have been introduced, the friability according to this test being a percentage of powder not retained after the test on a sieve with a mesh size of 100 microns;

(b) an apparent density, for a particle size cut within the range of about 100 to about 200 microns, of between about 300 and about 525 g/l;

(c) less than approximately 30% of particles with a size within the range of about 0 and about 75 microns; and (d) a rate of dissolution according to a Test II of between about 0 and about 30 seconds, said Test II comprising introducing into about 150 g of demineralized and degassed water maintained at about 20° C. and subjected to stirring at 200 rpm in a 250 ml low form beaker, exactly 5 g of a particle size cut, within the range of about 100 and 200 microns, of the powder to be tested, the rate of dissolution being the time necessary after introduction of the particle size cut to obtain perfect visual clarity of the suspension thus prepared.

2. Pulverulent mannitol according to claim 1, wherein less than about 40% of the particles have a size within the range of about 250 microns and about 315 microns.

3. Pulverulent mannitol according to claim 2, wherein less than about 30% of the particles have a size within the range of about 250 microns and about 315 microns.

4. Pulverulent mannitol according to claim 3, wherein less than about 20% of the particles have a size within the range of about 250 microns and about 315 microns.

5. Pulverulent mannitol according to claim 1, wherein the friability according to Test I comprises between about 40% and about 68%.

6. Pulverulent mannitol according to claim 5, wherein the friability according to Test I comprises between about 45% and about 65%.

7. Pulverulent mannitol according to claim 1, wherein the apparent density is between about 350 to about 510 g/l.

8. Pulverulent mannitol according to claim 7, wherein the apparent density is between about 400 to about 495 g/l.

9. Pulverulent mannitol according to claim 1, comprising a uniformity of particle size distribution of between about 1 and about 8.

10. Pulverulent mannitol according to claim 9, comprising a uniformity of particle size distribution of between about 1 and about 5.

11. Pulverulent mannitol according to claim 10, comprising a uniformity of particle size distribution of between about 1 and about 3.

12. Pulverulent mannitol according to claim 1, wherein the size of the particles of pulverulent mannitol comprise a mean diameter of particle size between about 100 and about 200 microns.

13. Pulverulent mannitol according to claim 1, wherein no more than about 10% of the particles have a size within the range of about 0 and about 75 microns.

14. Pulverulent mannitol according to claim 13, wherein no more than about 5% of the particles have a size within the range of about 0 and about 75 microns.

15. Pulverulent mannitol according to claim 1, being essentially devoid of particles with a size within the range of about 0 and about 40 microns and of particles with a size greater than 315 microns.

16. Pulverulent mannitol according to claim 1, comprising a mannitol richness, calculated with respect to an amount of at least one member selected from a group consisting of sugars and polyols, greater than approximately 90%.

17. Pulverulent mannitol according to claim 16, wherein the mannitol richness is greater than approximately 95%.

18. Pulverulent mannitol according to claim 17, wherein the mannitol richness is greater than approximately 98.5%.

19. Pulverulent mannitol according to claim 1, wherein the rate of dissolution is between about 0 and about 25 seconds.

20. Pulverulent mannitol according to claim 1, comprising a characteristic selected from a group consisting of a Carr Index of between about 70 and about 90.

21. Pulverulent mannitol according to claim 20, wherein the Carr Index is between about 75 and about 90.

22. Pulverulent mannitol according to claim 21, wherein the Carr Index is between about 80 and about 90.

23. Process for the preparation of pulverulent mannitol comprising:

atomizing a mannitol fluid selected from a group consisting of a mannitol solution and a mannitol suspension, said mannitol fluid comprising a solid content of between about 20 and about 70% solids, and mannitol with a richness greater than about 90% to result in atomized mannitol fluid; and granulating by a wet route the atomized mannitol fluid to result in the pulverulent mannitol of claim 1.

24. Compositions intended for the food and pharmaceutical fields, comprising the pulverulent mannitol according to claim 1, used as sweetening agent, texturing agent, additive excipient, or additive vehicle.

25. A composition comprising a sweetening agent, said sweetening agent comprising the pulverulent mannitol according to claim 1.

26. A composition comprising a texturing agent, said texturing agent comprising the pulverulent mannitol according to claim 1.

27. A composition comprising an additive excipient, said additive excipient comprising the pulverulent mannitol according to claim 1.

28. A composition comprising an additive vehicle, said additive vehicle comprising the pulverulent mannitol according to claim 1.

* * * * *